(12) United States Patent
Williams et al.

(10) Patent No.: US 6,342,628 B1
(45) Date of Patent: Jan. 29, 2002

(54) PROCESS FOR THE PRODUCTION OF VINYL ACETATE

(75) Inventors: Bruce Leo Williams, Elloughton; Robert William Clarke, Driffield; Timothy Crispin Bristow, Beverley; Michael James Baker, Feltham, all of (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/363,012

(22) Filed: Jul. 29, 1999

(30) Foreign Application Priority Data

Aug. 11, 1998 (GB) .............................................. 9817362

(51) Int. Cl.⁷ .............................................. C07C 67/05
(52) U.S. Cl. ...................................... 560/245; 560/243
(58) Field of Search ................................... 560/243, 245

(56) References Cited

U.S. PATENT DOCUMENTS 3,862,216 A * 1/1975 Calcagno et al.
5,550,281 A * 8/1996 Cirjak et al.
5,817,866 A * 10/1998 Bristow et al.

FOREIGN PATENT DOCUMENTS

| CA | 1156674 | 12/1979 |
| EP | 0464633 A | 6/1991 |
| EP | 0685449 A | 2/1995 |
| EP | 0 847 982 A1 | 6/1998 |

OTHER PUBLICATIONS

J. M Davidson et al., Front. Chem. React. Eng., 1984, (1) pp. 300–313, Selectivity Problems and Kinetic Models in the Palladium Catalysed Oxidation of Ethene and Acetic Acid to Ethenyl Acetate. Related Reactions of Propene, 1–Butene and 1–Hexene.

R Abel et al., Chem.Eng. Technol. 17 (1994) pp 112–118, "Deviation of a Vinyl Acetate Catalyst".

Nakamura and Yasui, Journal of Catalysts 17, (1970), pp. 366–374, "The Mechanism of the palladium–Catalyzed Synthesis of Vinyl Acetate from Ethylene in a Heterogeneous Gas Reaction".

Samanos et al, J. Catal. 23, (1971), pp. 19–30, "The Mechanism of Vinyl Acetate Formation by Gas–Phase Catalytic Ethylene Acetoxidation".

R. S. Shetty and S. B. Chandalia, Metals and Minerals Review, Dec., 1970, 10(1) pp 35–40, "Vapour phase reaction of Ethylene to Vinyl Acetate".

R. Van Helden et al., Rec. Trav. Chim.Pays–Bas(1968), 87 (10) PP 961–91.

* cited by examiner

*Primary Examiner*—Gary Geist
*Assistant Examiner*—Robert W. Deemie
(74) *Attorney, Agent, or Firm*—Nixon & Vanderhye (57) ABSTRACT

In a process for production of vinyl acetate by the reaction of ethylene, acetic acid and oxygen, ethylene is recovered from the gases withdrawn from the reactor and recycled such that the amount of ethylene in the combined feed to the reactor is at least 60 mol %.

20 Claims, 5 Drawing Sheets

PROCESS FOR THE PRODUCTION OF VINYL ACETATE

BACKGROUND OF THE INVENTION

The present invention relates to a process for the production of vinyl acetate.

Vinyl acetate may be produced by the acetoxylation of ethylene in the presence of a palladium-containing catalyst. In addition to vinyl acetate, carbon dioxide is produced as a by-product.

In commercial operation, vinyl acetate product and unreacted ethylene are recovered from the gases exiting the reaction vessel. The unreacted ethylene is recycled, together with fresh ethylene to the reaction vessel. The recycled ethylene contains some carbon dioxide and other by-products as well as some inert gases such as nitrogen and/or argon. The presence of these components limits the concentration of ethylene in the feed to the reaction vessel.

The factors which influence the selectivity of the process towards vinyl acetate are not fully understood. The general view taken by those skilled in the art is that once the concentration of ethylene in the reactant mixture exceeds a threshold value, the rate of formation of vinyl acetate becomes independent of the concentration of ethylene. The rationale behind this view is that even if ethylene is involved in the rate determining step, the rate of formation of vinyl acetate with respect to ethylene will tend to zero once an amount greater than the stoichiometric amount of ethylene is exceeded. In other words, as long as an excess of ethylene is present in the reactant mixture, the magnitude of this excess should not have a bearing on the amount of vinyl acetate produced.

This general view or technical prejudice is supported by experimental data in Davidson et al. (Front. Chem. React. Eng., 1984, (1) 300–313). The data show that in acetoxylation reactions carried out at atmospheric pressure, the amount of vinyl acetate produced remains substantially constant as the ethylene concentration is increased between 31.6 mol % to 47.4 mol %.

The technical prejudice also extends to acetoxylation reactions performed above atmospheric pressure. In Abel et al. (Chem. Eng. Technol. 17 (1994) 112–118), ethylene, acetic acid and oxygen are reacted together at a total pressure of 8 barg. The document recites that the rate of formation of vinyl acetate is independent of the concentration of ethylene in the reaction mixture, provided that the concentration of ethylene exiting the reactor is above 30 mol %. To ensure that the effluent concentration exceeds this value, ethylene feed concentrations of 57 mol % are employed.

R S Shetty and S B Chandalia in Metals and Minerals Review December 1970 35–40 propose that in an industrial process an ethylene concentration of more than about 65% may be chosen to keep outside the explosive limit. However in an experiment using a gas mixture containing a mole ratio of ethylene to oxygen of 69.3:30.7 the catalyst activity changed rapidly with time. Furthermore, the concentration of acetic acid and hence the ethylene concentration is not apparent. Neither is it apparent whether ethylene was recovered and recycled.

Nakamura et al in J. Catal. 17 (1970) 366–374 describes the effect of potassium acetate on the catalytic activity of a palladium catalyst with a feed gas of ethylene: oxygen: acetic acid of 80:10:10 (FIG. 4). However it is not apparent that ethylene was recycled nor is any beneficial effect of high ethylene concentration described.

Samanos et al in J Catal. (1971) 23 19–30 describe the rate of reaction forming vinyl acetate varying linearly with ethylene partial pressure whilst the rate at which carbon dioxide is formed remains constant. However, it is not apparent the ethylene is recovered and recycled in the experiment.

DESCRIPTION OF THE INVENTION

We have now found that when vinyl acetate is produced above atmospheric pressure, the selectivity towards vinyl acetate increases as the concentration of ethylene in the reactant mixture is increased above 60 mol %. This finding is contrary to the technical prejudice in the art.

Accordingly, the present invention provides a process for the production of vinyl acetate, said process comprising the steps of:

(a) introducing ethylene, acetic acid and an oxygen containing gas into a reactor, (b) reacting said ethylene, acetic acid, and oxygen-containing gas in the presence of a catalyst material in said reactor to produce vinyl acetate at above atmospheric pressure, (c) withdrawing from said reactor gases comprising unreacted ethylene, vinyl acetate, carbon dioxide by product and inert gases such as nitrogen and/or argon;

(d) recovering from the gases withdrawn from said reactor, unreacted ethylene optionally together with minor amounts of said carbon dioxide and inert gases, and (e) introducing the recovered ethylene from step (d) and additional ethylene to said reactor in step (a) wherein the amount of ethylene in the combined feed to the reactor is at least 60 mol %.

Preferably also, the method further comprises the step of recovering the vinyl acetate produced.

The present invention provides a novel and cost effective route for the production of vinyl acetate at above atmospheric pressure, 0 Pa gauge (0 barg). The reaction may be carried out at a pressure of between $5 \times 10^4$ Pa gauge (0.5 barg) and $2 \times 10^6$ Pa gauge (20 barg), preferably between $6 \times 10^5$ Pa gauge (6 barg) and $1.4 \times 10^6$ Pa gauge (14 barg) and, most preferably, between $7 \times 10^5$ Pa gauge (7 barg) and $1.2 \times 10^6$ Pa gauge (12 barg). These pressure conditions are believe to affect the intersection between ethylene and the surface of the catalyst such that an increase in selectivity towards the production of vinyl acetate is observed when the amount of ethylene in the feed is increased above 60 mol%. This effect is surprising: the rate of vinyl acetate production with respect to ethylene is expected to be of zero order once an initial ethylene concentration of at least 57 mol % is employed as taught in Abel et al. (Chem. Eng. Technol. 17 (1994) 112–118).

Whilst we do not wish to be bound to theory, the increase in selectivity may be explained by a combination of two factors. In addition to increasing the amount of vinyl acetate produced, an increase in the amount of ethylene in the feed is also found to reduce the amount of carbon dioxide produced as a by-product. This in turn, can reduce the amount of carbon dioxide which has to be separated from the recovered unreacted ethylene and/or the amount of carbon dioxide recycled to the reactor with the recovered ethylene.

The catalyst of the present invention may be fixed-bed or fluid-bed catalyst. Preferably, a fluid-bed catalyst is employed in a fluid bed reactor.

The catalyst suitably comprises a Group VIII metal and a promoter. Preferably, the catalyst further comprises a co-promoter. These compounds are suitably accommodated on a support.

With regards to the Group VIII metal, the preferred metal is palladium. The metal may be present in a concentration of greater than 0.2% by weight, preferably greater than 0.5% by weight, especially about 1% by weight based upon total weight of catalyst. The metal concentration may be as high as 10% by weight. Suitable sources of palladium include palladium (II) chloride, sodium or potassium tetrachloropalladate (II) ($Na_2PdCl_4$ or $K_2PdCl_4$), palladium acetate, palladium (II) nitrate, $H_2PdCl_4$ or palladium (II) sulphate.

In addition to the Group VIII metal, the catalyst comprises a promoter. Suitable promoters include gold, copper and/or nickel. A preferred promoter is gold. Suitable sources of gold include gold chloride, tetrachloroauric acid ($HAuCl_4$), $NaAuCl_4$, $KAuCl_4$, dimethyl gold acetate, barium acetoaurate or gold acetate. The preferred gold compound is $HAuCl_4$. The promoter metal may be present in an amount of from 0.1 to 10% by weight in the finished catalyst.

The catalyst composition may comprise a co-promoter material. Suitable co-promoters include Group I, Group II, lanthanide or transition metals for example cadmium, barium, potassium, sodium, iron, manganese, nickel, antimony, and/or lanthanum, which are present in the finished catalyst as salts, e.g. an acetate salt. The preferred salts are potassium or sodium acetate. The co-promoter may be present in the catalyst composition in a concentration of up to 15%. Where the catalyst is a fixed bed catalyst, the co-promoter concentration is preferably between 3 and 11 wt %. Where the catalyst is a fluid bed catalyst, and the acetic acid is introduced into the reactor in the liquid form, the co-promoter may be present in a concentration of up to 6 wt %, preferably between 3.5 to 5.5 wt % especially 5 wt %. Where the catalyst is a fluid bed catalyst and the acetic acid is introduced into the reactor in vapour form, the co-promoter may be present in a concentration of up to 11 wt % of the total catalyst.

The activity of the catalyst may decrease with time. In particular, due to the volatile nature of the co-promoter, the level of co-promoter in the catalyst material decreases with time, thus resulting in loss of catalyst activity. In order to maintain a constant concentration of co-promoter in the catalyst, fresh co-promoter may be added to the catalyst during the reaction. This may suitably be carried out by adding the co-promoter material to the liquid acetic acid feed or to the liquid recycle acetic acid. Alternatively, the additional co-promoter may be introduced as a solution e.g. in water or in acid directly by spraying through a suitable injection means such as a nozzle.

The catalyst material is a supported catalyst. Suitable catalyst supports include porous silica, alumina, silica/alumina, silica/titania, titania, zirconia or carbon. Preferably the support is silica. Suitably, the support may have a pore volume from 0.2 to 3.5 mL per gram of support, a surface area of 5 to 800 $m^2$ per gram of support and an apparent bulk density of 0.3 to 1.5 g.mL. The support may typically have a particle size distribution such that at least 60% of the catalyst particles have a particle diameter of below $2\times10^{-4}$m (200 microns). Preferably at least 50%, more preferably at least 80% and most preferably at least 90% of the catalyst particles have a particle diameter less than $1.05\times10^{-4}$m (105 microns). Preferably no more than 40% of the catalyst particles have a diameter of less than $4\times10^{-5}$m (40 microns).

The catalyst may be prepared by any suitable method. Suitably, the first stage of the catalyst preparation process involves impregnation of the support material with a solution containing the required Group VIII metal and the promoter metal in the form of soluble salts. Examples of such salts are soluble halide derivatives. The impregnating solution is preferably an aqueous solution and the volume of solution used is such that it corresponds to between 50 and 100% of the pore volume of the support, preferably 50 to 99% of the pore volume.

The impregnated support is dried at ambient or reduced pressure and from ambient temperature to 150° C., preferably 60 to 130° C. prior to metals reduction. To convert such materials into the metallic state, the impregnated support is treated with a reducing agent such as ethylene, hydrazine, formaldehyde or hydrogen. If hydrogen is used, it will usually be necessary to heat the catalyst to 100 to 850° C. in order to effect complete reduction.

After the steps described above have been carried out, the reduced catalyst is washed with water and then dried. The dried carrier is then impregnated with the required amount of co-promoter and thereafter dried. Alternatively, the wet, reduced, washed material is impregnated with co-promoter then dried.

The method of catalyst preparation may be varied to optimise catalyst performance based on maximising vinyl acetate yield and selectivity.

The process of the present invention comprises reacting ethylene, liquid acetic acid and an oxygen-containing gas in the presence of the catalyst material. Ethylene may be used in substantially pure form or admixed with one or more of nitrogen, methane, ethane, carbon dioxide and water in the form of steam or one or more of hydrogen, $C_3/C_4$ alkenes or alkanes.

The amount of ethylene in the combined feed to the reactor is at least 60 mol %. The upper limit to the ethylene concentration in the combined feeds is determined by a number of factors including (a) the need to have oxygen and acetic acid reactants in the feed and (b) the loss of ethylene in gas purge from the reactor to remove carbon dioxide and other by-products, and inert gases such as nitrogen and/or argon. Suitably, the amount of ethylene in the combined feed is up to 85 mol %. Preferably, the amount of ethylene in the combined feed is in the range at least 60 mol % to 80 mol %.

Operating with higher ethylene concentrations can lead to an increased loss of ethylene in the gases vented from the reaction system to remove carbon dioxide and inerts. However, if the amount of inerts in the system can be reduced, the amount of purge gas which has to be vented can be reduced and hence the loss of ethylene can also be reduced. The need to vent purge gas from the reactor to remove inert gases such as nitrogen and/or argon may be reduced in one or more of the following ways:

Reduce/minimise inerts such as nitrogen, methane and ethane in the ethylene feed gas.

Reduce/minimise inerts such as nitrogen and argon in the oxygen feed gas.

Reduce/minimise inerts such as dissolved nitrogen in the acetic acid feed.

Reduce/eliminate inert gas purges to instruments, for example by using ethylene or carbon dioxide purges.

Use carbon dioxide as purge gas.

Reduce/minimise inerts from catalyst transfer operations or use ethylene or carbon dioxide.

Reduce/eliminate leakage of nitrogen into the oxygen via sparger purge system.

Reduce/eliminate air leakage into the vacuum system of product recovery.

Reduce/minimise inerts in water used in the off-gas prescrubber prior to the carbon dioxide removal system (Benfield).

Design the oxygen injection system to reduce/minimise the use of inert gas.

The oxygen-containing gas may suitably be air or a gas richer or poorer in molecular oxygen than air. Suitably, the gas may be oxygen diluted with a suitable diluent, for example, nitrogen, argon or carbon dioxide. Preferably the gas is oxygen. The amount of oxygen in the combined feed to the reactor is determined by factors such as conversion and the flammability limits of the gases exiting the reactor. Preferably, the amount of oxygen is the combined feed to the reactor is in the range 4 to 15 mol %, suitably 4 to 12 mol%.

The acetic acid may be introduced into the reactor in liquid form. Optionally, some acetic acid may be introduced in the vapour form. The acetic acid need not be highly purified, that is it may be crude acetic acid. Suitably, the liquid acetic acid may be introduced into the fluid bed reactor by any suitable injection means, for example by a nozzle in which a gas is used to assist in the atomisation of the liquid or, liquid-only spray-type nozzles may be used. Additionally, recycled acetic acid may be introduced into the reactor. The re-cycled acetic acid optionally containing small amounts of water may be pre-mixed with the crude acetic acid or may be introduced into the reactor using a separate injection means. Suitably the amount of acetic acid in the combined feed to the reactor is in the range of 10 to 20 mol % and the amount of water is less than 6 wt%, preferably less than 4 wt%, more preferably less than 3 wt% of the total of acetic acid and water entering the reactor.

The process is carried out in a reactor and may suitably be operated at a temperature of from 100 to 400° C., preferably 140 to 210° C.

The process may be carried out in a fixed bed or fluid bed reactor.

The unreacted ethylene may be recovered from the gases withdrawn from the reactor by the steps of (i) separating condensable products from the gases by condensation and (ii) treating the gases from step (i) to recover ethylene, for example by membrane separation or chemical treatment. The condensable products may be separated from the withdrawn gases by condensation for example by using a heat exchanger or by quenching the gases by flowing counter to a flow of liquid acetic acid and/or condensable products which absorbs the vinyl acetate product.

Chemical treatment may comprise the steps of (a') contacting the gases from step (i) with acetic acid in a scrubber to remove residual vinyl acetate product; (b') treating the product of step (a') with water in a scrubber to remove acetic acid and (c') removing carbon dioxide from the ethylene in the product for step (b') by contacting with potassium carbonate. A Benfield system may be used.

BRIEF DESCRIPTION OF THE DRAWINGS

These and other aspects of the present invention will now be described with reference to the following Experiments and accompanying Figures in which.

EXAMPLES

Experiment 1

(a) Preparation of the Fluid Bed Catalyst Support

A microspheroidal silica support was prepared by spray-drying a mixture of Nalco silica sol 1060 (obtained from Nalco Chemical Company) and Degussa Aerosil ® silica (obtained from Degussa Chemical Company). In the dried support, 80% of the silica came from the sol and 20% of the silica came from the Aerosil ®. The spray-dried microspheres were calcined in air at 640° C. for 4 hours.

The particle size distribution of the support is as follows:

| Particle Size (microns) | % |
|---|---|
| >3 × $10^{-4}$ m(>300) | 2 |
| 4.4 × $10^{-5}$ m − 3 × $10^{-4}$ m(44 − 300) | 68 |
| <4.4 × $10^{-5}$ m(<44) | 30 |

It should be understood that the particle size distribution given above is not intended to be limiting and that variations in this distribution are contemplated depending upon reactor size and operating conditions.

(b) Preparation of Catalyst

The silica support above (1.0kg) was impregnated with a solution of $Na_2PdCl_4.xH_2O$ (containing 21.4g Pd) and $HAuCl_4.xH_2O$ (containing 7.23gAu) in distilled $H_2O$ by incipient wetness. The resulting mixture was mixed thoroughly, left to stand for one hour and dried overnight.

The impregnated material was then added slowly to a 2% solution of $N_2H_4$ in distilled water and the mixture was allowed to stand with occasional stirring. Thereafter, the mixture was filtered and washed with 4×8.3 litres distilled $H_2O$. The solid was then dried overnight.

The material was impregnated with an aqueous solution of KOAc (76.7g) by incipient wetness. The resulting mixture was mixed thoroughly, left to stand for 1 hour and dried overnight.

(c) Preparation of Vinyl Acetate

Figure 1:
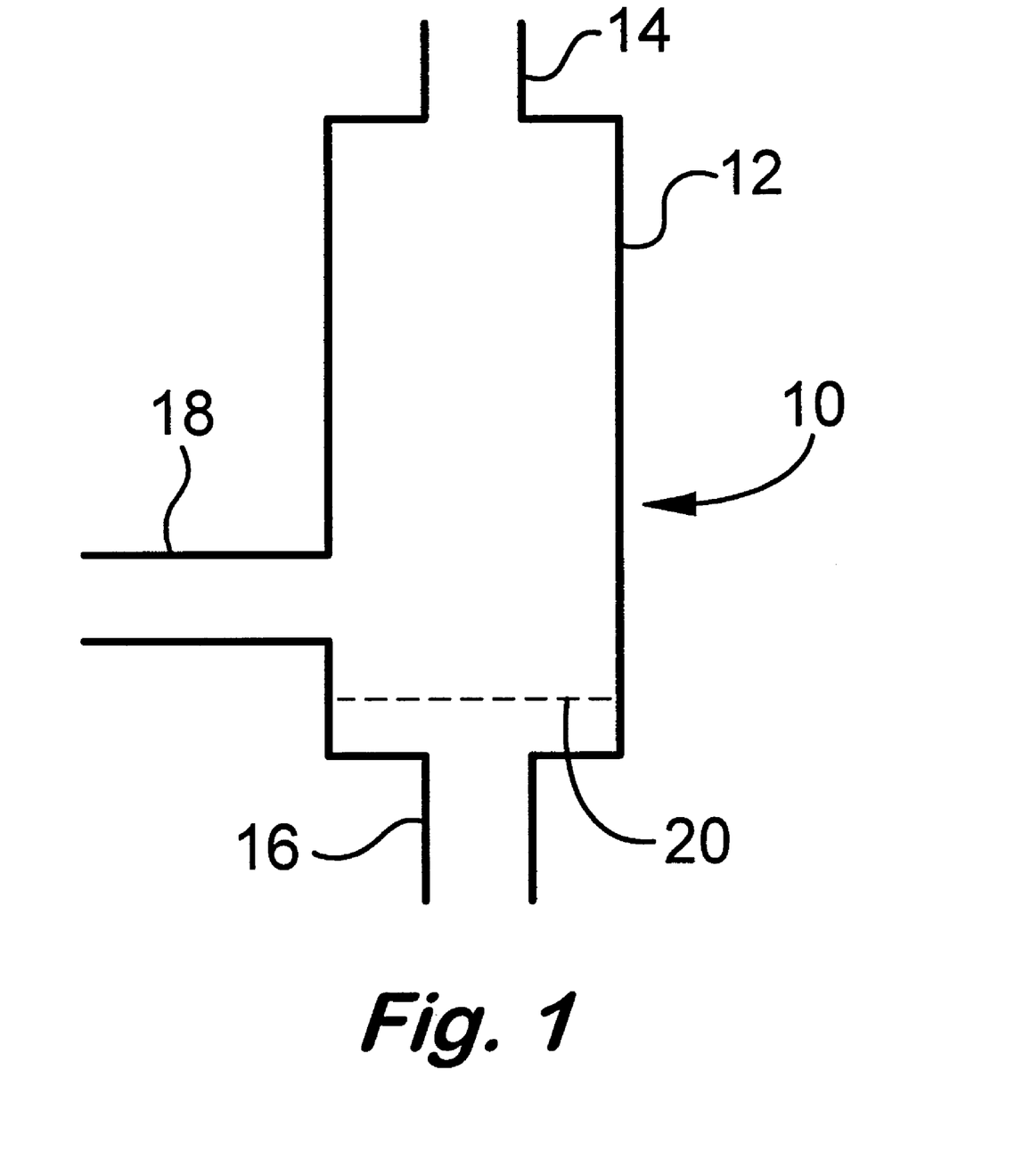
FIG. 1 is a schematic diagram of a fluid bed reactor for use in a preferred embodiment of the present invention.

Vinyl acetate was produced using a 0.0381 m (1.5") diameter fluid bed reactor. A schematic diagram of the reactor is shown in FIG. 1 below.

The reactor 10 defines a tubular housing 12 having an outlet 14, and first and second inlets 16, 18. The reactor 10 further comprises a sintered grid plate 20 positioned within the housing 12.

In operation, the reactor 10 is charged with 300g of a fluid bed catalyst to form a fluid bed. Feed gas comprising ethylene, nitrogen, oxygen, vaporised acetic acid, and optionally vapourised water is introduced into the reactor 10 via the first inlet 16. Oxygen and/or nitrogen is introduced into the reactor 10 via the second inlet 18.

The flow of gas through the inlets 16, 18 is controlled by mass flow controllers (not shown). Acetic acid is fed into the reactor 10 at a rate of 273 g/hour. Oxygen is introduced via the first and second inlets 16, 18 such that the total rate of oxygen into the reactor 10 is 83.3g/hour. The flow of ethylene is varied as shown in Table 1. A constant volumetric gas throughput is maintained by adjusting the flow of nitrogen accordingly.

The pressure in the reactor 10 is controlled at 8 barg and the reactor temperature is maintained at 152° C. (measured at 6 points within the fluid bed). All lines (not shown) leading to and from the reactor 10 are heated and maintained at 160° C. to prevent the reactor feeds and/or products from condensing therein.

The gaseous effluent is analysed on-line using a Chrompack Model CP9000 gas chromatograph equipped with both Flame Ionisation Detector(s) (FID) and Thermal Conductivity Detector(s) (TCD). Ethylene and carbon dioxide are separated using a Poraplot U column and quantified by TCD. Oxygen and nitrogen are separated on a molecular sieve column and quantified by TCD. Vinyl acetate and acetic acid and other by-products are separated on a DB 1701 capillary column and quantified with FID.

Results and Discussion

The results of Experiment 1 are shown in Table 1 below.

TABLE 1

| Example | Mol % Ethylene in feed | g/hr Ethylene in feed | g/hr Nitrogen in feed | g VA/hr in product | g $CO_2$/hr in product | g VA/kg – cat/hr (1) | % VA Selectivity (2) |
|---|---|---|---|---|---|---|---|
| 1* | 20 | 175 | 503 | 118 | 25.9 | 393 | 82.3 |
| 2* | 28 | 246 | 433 | 135 | 22.7 | 449 | 85.8 |
| 3* | 36 | 316 | 362 | 141 | 21.0 | 471 | 87.3 |
| 4* | 40 | 353 | 326 | 149 | 20.7 | 496 | 88.0 |
| 5* | 40 | 353 | 326 | 151 | 20.8 | 503 | 88.1 |
| 6* | 44 | 387 | 292 | 148 | 19.8 | 495 | 88.5 |
| 7* | 52 | 458 | 222 | 158 | 18.4 | 525 | 89.7 |
| 8 | 60 | 528 | 151 | 164 | 18.5 | 548 | 90.1 |

*comparative examples
(1) grams of vinyl acetate produced per kilogram of catalyst per hour.
(2) VA selectivity = VA/(VA + ½$CO_2$).

Figure 2:
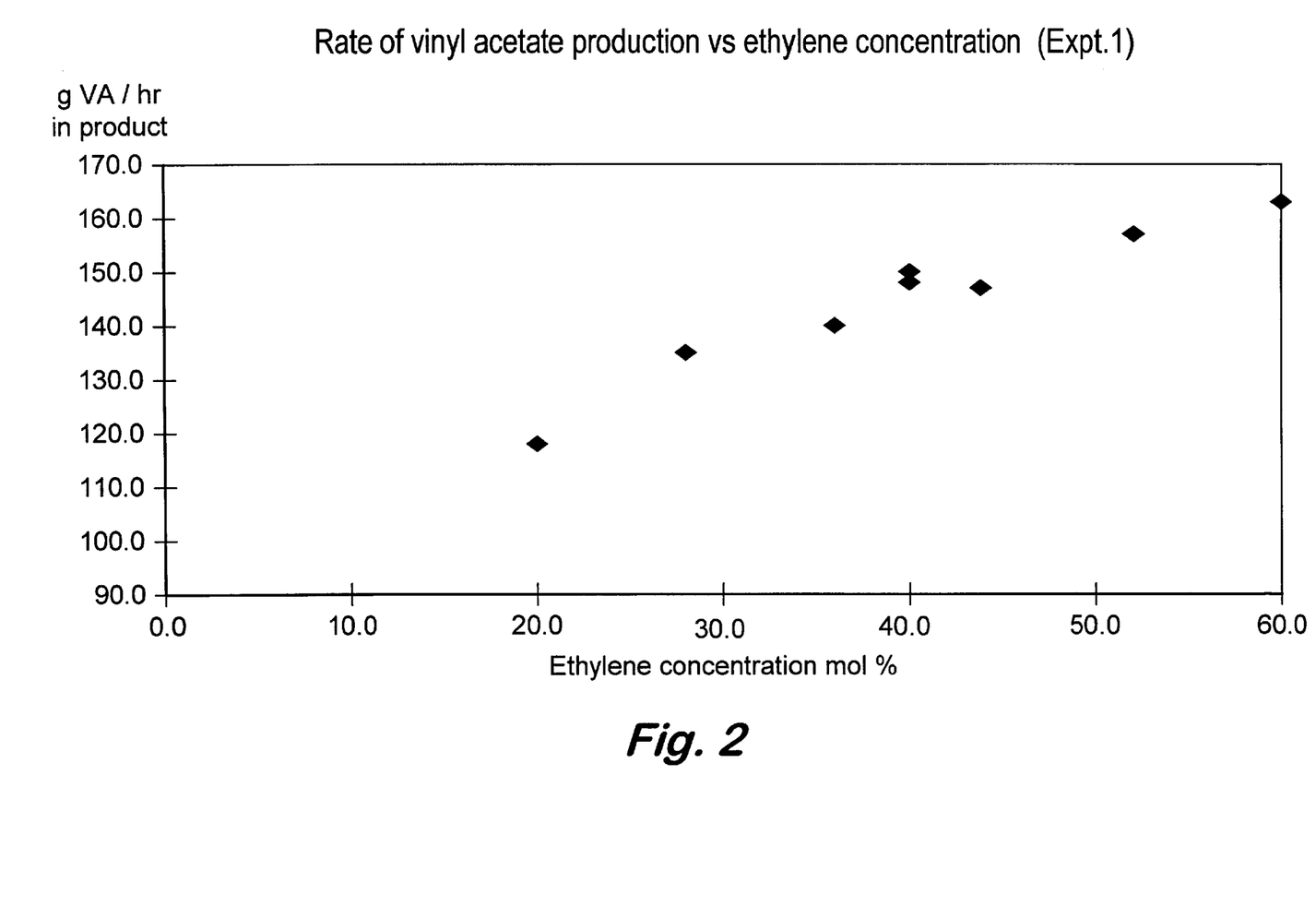
FIG. 2 is a plot of the rate of vinyl acetate production versus ethylene concentration for Experiment 1.

FIG. 2 shows how the rate of vinyl acetate produced varies as the concentration of ethylene in the feed composition increases. The graph shows that as the ethylene concentration is increased from 20 mol % to 60 mol %, the rate of vinyl acetate production increases.

Figure 3:
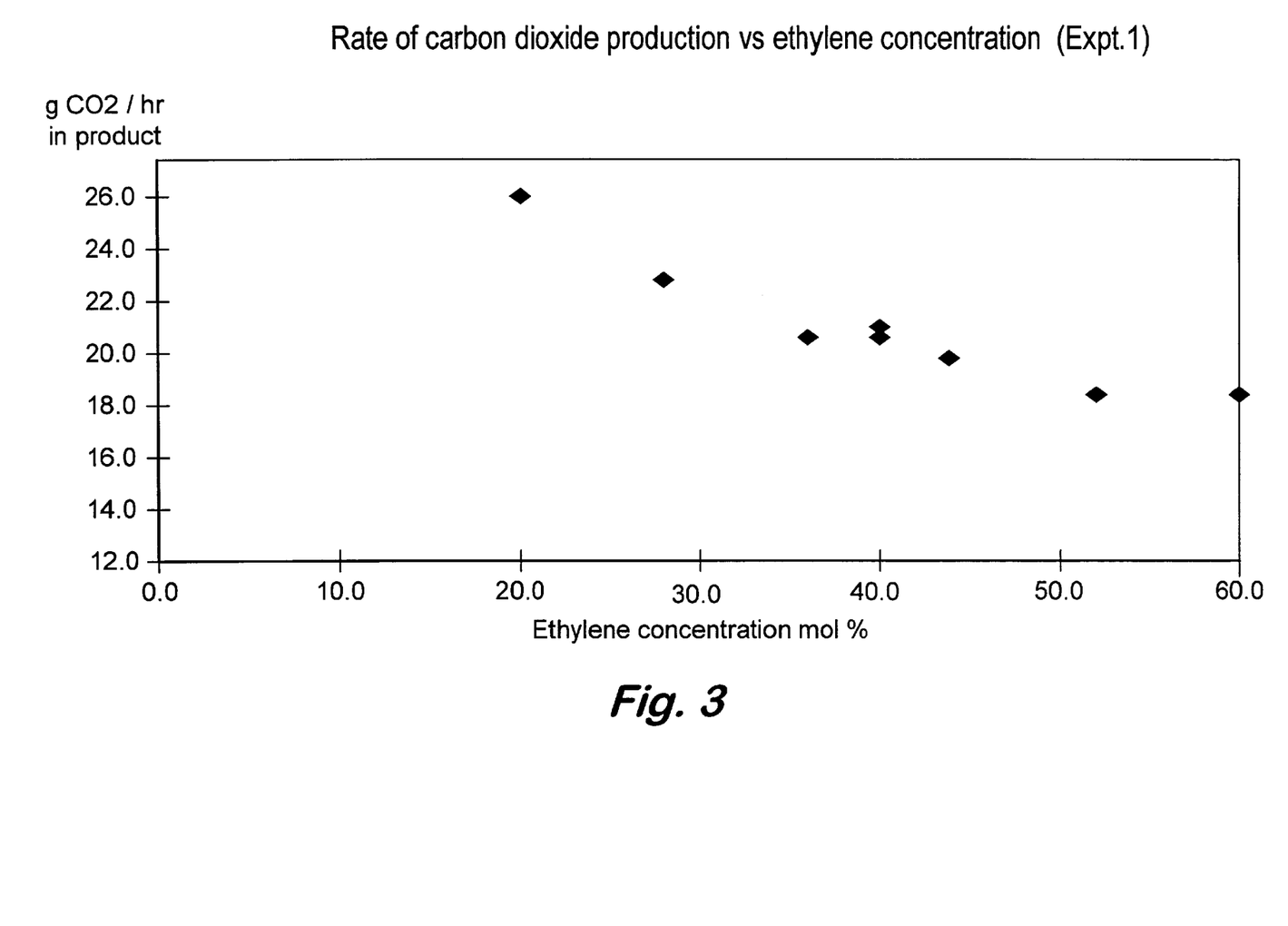
FIG. 3 is a plot of the rate of carbon dioxide production versus ethylene concentration for Experiment 1.

FIG. 3 shows how the rate of production of carbon dioxide varies as the concentration of ethylene in the feed composition increases. The graph shows that as the ethylene concentration is increased from 20 mol% to 60 mol%, the rate of carbon dioxide decreases.

Figure 4:
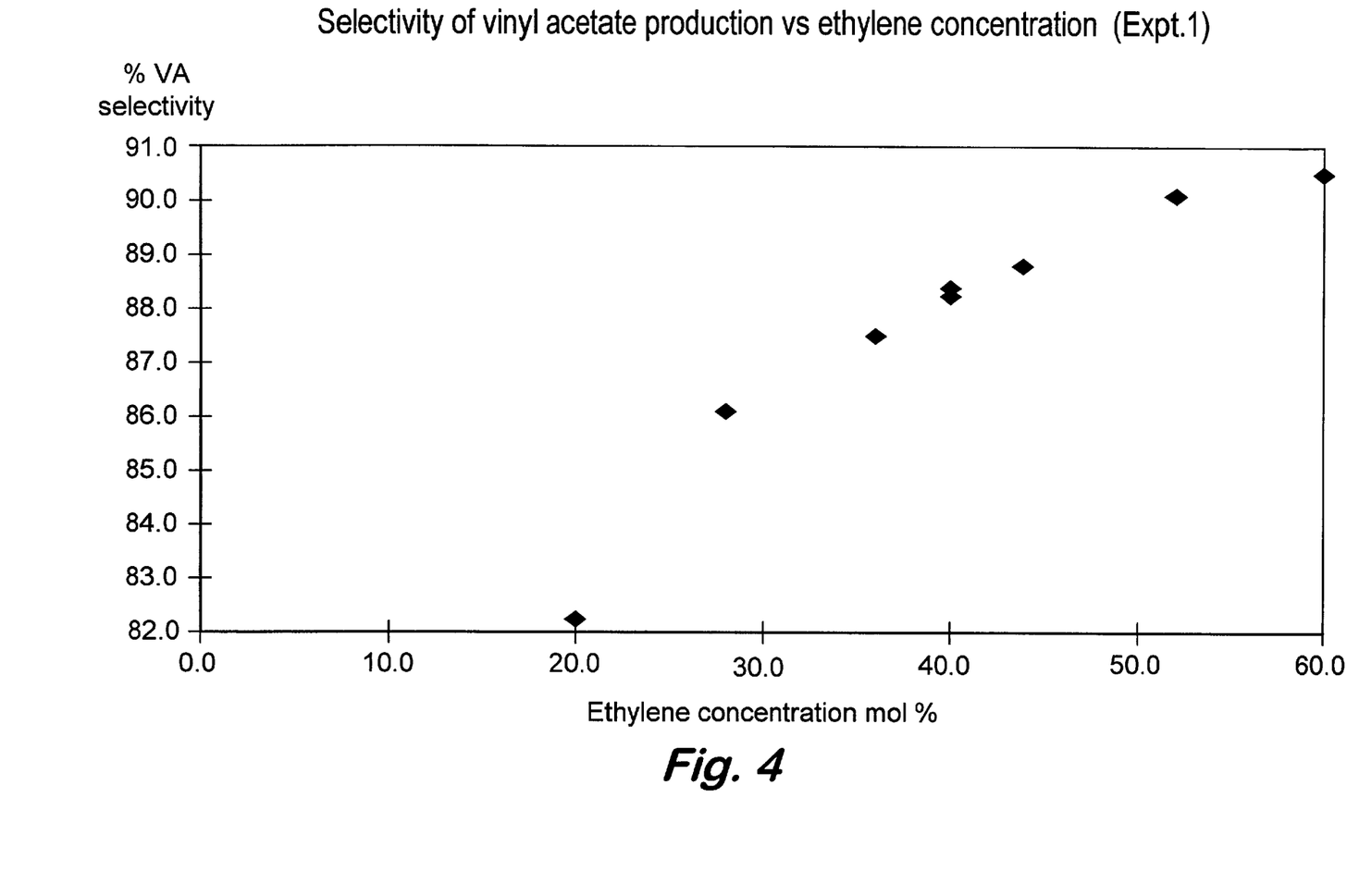
FIG. 4 is a plot of the selectivity of vinyl acetate production versus ethylene concentration for Experiment 1.

FIG. 4 shows how the selectivity of the process becomes increasingly selective towards the production of vinyl acetate as the concentration of ethylene is increased.

The fluid bed catalyst support (54.4kg) is impregnated with a solution of $Na_2PdCl_4 \cdot xH_2O$ (containing 1000g Pd) and $HAuCl_4 \cdot xH_2O$ (containing 400g Au) in distilled $H_2O$ by incipient wetness. The resulting mixture was mixed thoroughly, left to stand for one hour and dried overnight.

A portion of the impregnated material (18kg) is added slowly to a 5% solution of $N_2H_4$ in distilled water. The mixture was allowed to stand with occasional stirring. Thereafter the mixture was filtered and washed with 4×200 litres distilled $H_2O$. The solid was then dried overnight.

The material was impregnated with an aqueous solution of KOAc (1.3kg) by incipient wetness. The resulting mixture was mixed thoroughly, left to stand for 1 hour and dried overnight.

(c) Preparation of Vinyl Acetate

Vinyl acetate is prepared using the 0.0381 m (1.5") diameter fluid bed reactor of Experiment 1 above. Acetic acid is introduced into the reactor 10 at a rate of 227g/hour, and oxygen is introduced at a rate of 83.3g/hour.

Results and Discussion

The results of Experiment 2 are shown in Table 2 below.

TABLE 2

| Example | Mol % Ethylene in feed | g/hr Ethylene in feed | g/hr Nitrogen in feed | g VA/hr in product | g $CO_2$/hr in product | g VA/kg – cat/hr (1) | % VA Selectivity (2) |
|---|---|---|---|---|---|---|---|
| 9 | 60 | 529 | 173 | 174 | 18.6 | 580 | 90.5 |
| 10 | 66 | 581 | 120 | 169 | 17.4 | 562 | 90.8 |
| 11 | 72 | 634 | 67.5 | 175 | 17.5 | 585 | 91.1 |
| 12 | 77.4 | 682 | 19.8 | 167 | 16.1 | 557 | 91.4 |
| 13 | 60 | 529 | 173 | 164 | 18.0 | 548 | 90.3 |
| 14* | 54 | 476 | 226 | 155 | 17.4 | 517 | 90.1 |
| 15* | 47 | 414 | 288 | 149 | 17.6 | 495 | 89.6 |
| 16* | 40 | 353 | 350 | 144 | 18.6 | 479 | 88.8 |
| 17 | 60 | 529 | 173 | 147 | 15.8 | 491 | 90.5 |

*comparative examples
(1) grams of vinyl acetate produced per kilogram of catalyst per hour.
(2) VA selectivity = VA/(VA + ½$CO_2$).

Experiment 2
(a) Preparation of the Fluid Bed Catalyst Support
In this Experiment, a fluid bed catalyst support prepared in accordance with Experiment 1 is employed.
(b) Preparation of Catalyst The results of Table 2 are listed in chronological order. As can be seen from a comparison of the results of Examples 9, 13 and 17, a notable decrease in catalytic activity is observed over the course of this Experiment. This catalyst deactivation means that the rates of vinyl acetate and carbon dioxide production of the examples cannot be directly compared.

Figure 5:
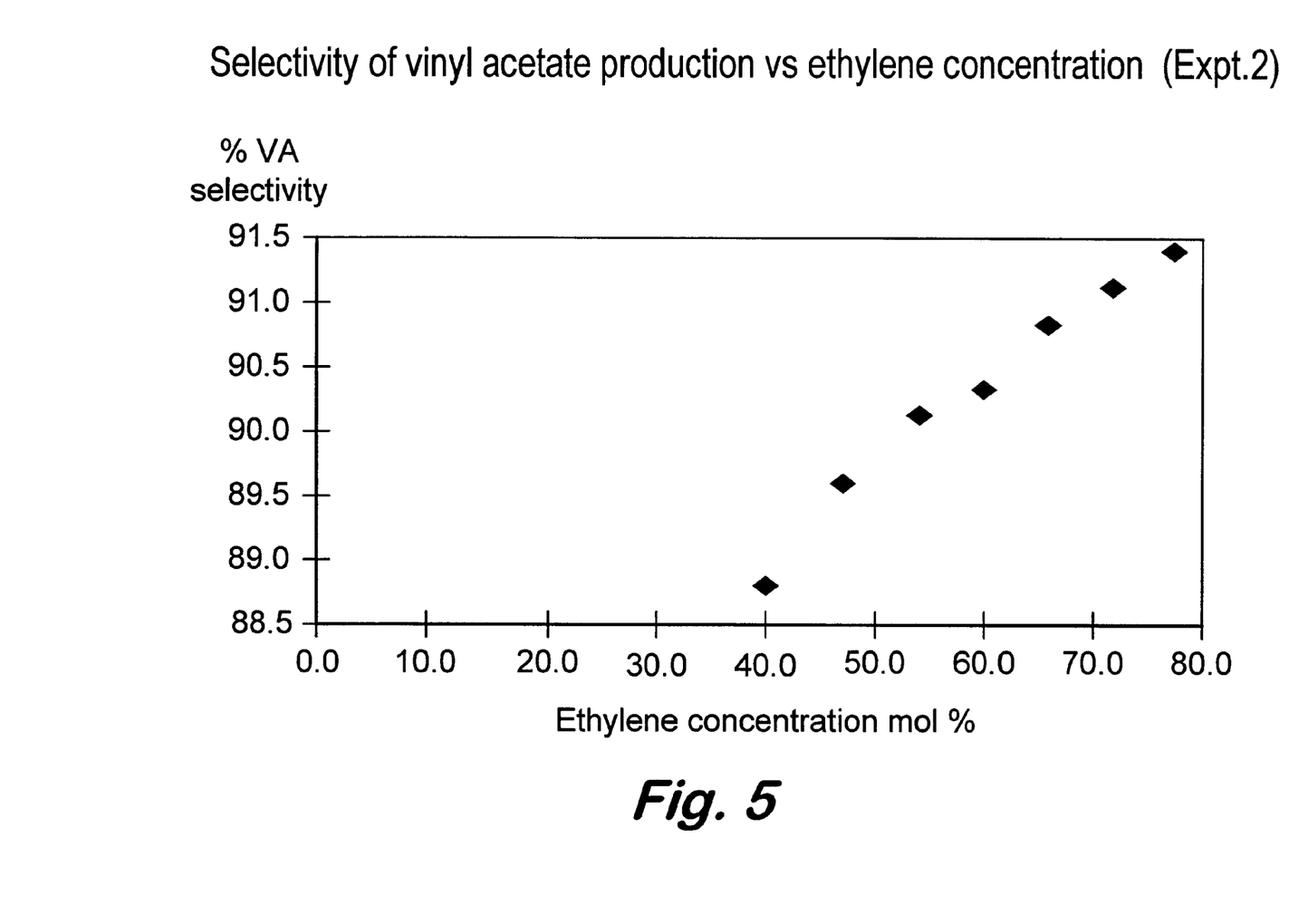
FIG. 5 is a plot of the selectivity of vinyl acetate production versus ethylene concentration for Experiment 2.

FIG. 5 shows how the selectivity of the process becomes increasingly selective towards the production of vinyl acetate as the concentration of ethylene is increased beyond 60 mol %.

We claim:

1. A process for the production of vinyl acetate, said process comprising the steps of:
   (a) introducing ethylene, acetic acid and an oxygen containing gas into a reactor;
   (b) reacting said ethylene, acetic acid, and oxygen-containing gas in the presence of a catalyst material in said reactor to produce vinyl acetate at above atmospheric pressure;
   (c) withdrawing from said reactor gases comprising unreacted ethylene, vinyl acetate, carbon dioxide by product and an inert gas;
   (d) recovering from the gases withdrawn from said reactor, unreacted ethylene optionally together with minor amounts of said carbon dioxide and inert gas; and
   (e) introducing the recovered ethylene from step (d) and additional ethylene to said reactor in step (a) wherein the amount of ethylene in the combined feed to the reactor is above 60 mol %, and up to 85 mol %.

2. A process as claimed in claim 1 in which ethylene is recovered from said gases withdrawn from said reactor by the steps of (i) separating condensable products from the gases and (ii) treating the gases from step (i) to recover ethylene by membrane separation or chemical treatment.

3. A process as claimed in claim 2 in which the condensable products are separated by use of a heat exchanger or by quenching the gases by flowing counter to a flow of liquid acetic acid and/or condensable products which absorbs the vinyl acetate product.

4. A process as claimed in claim 2 in which the chemical treatment comprises the steps of (a') contacting the gases from step (i) with acetic acid in a scrubber to remove residual vinyl acetate product; (b') treating the product of step (a') with water in a scrubber to remove acetic acid; and (c') removing carbon dioxide from the ethylene in the product from step (b') by contacting with potassium carbonate.

5. A process as claimed in claim 1 in which the amount of oxygen in the combined feed to the reactor is in the range 4 to 15 mol %.

6. A process as claimed in claim 1 in which the amount of acetic acid in the combined feed to the reactor is in the range 10 to 20 mol %.

7. A process as claimed in claim 5 in which the amount of acetic acid in the combined feed to the reactor is in the range 10 to 20 mol %.

8. A process as claimed in claim 1 in which the ethylene, acetic acid, and oxygen-containing gas are reacted in said reactor at a pressure of between 0.5 barg and 20 barg.

9. A process as claimed in claim 7 in which the ethylene, acetic acid, and oxygen-containing gas are reacted in said reactor at a pressure of between 0.5 barg and 20 barg.

10. A process as claimed in claim 1 in which said catalyst material comprises a Group VIII metal, preferably palladium, a promoter selected from the group consisting of gold, copper, nickel and mixtures thereof and optionally a co-promoter selected from the group consisting of Group I, Group II, lanthanide and transition metals.

11. A process as claimed in claim 9 in which said catalyst material comprises a Group VIII metal, preferably palladium, a promoter selected from the group consisting of gold, copper, nickel and mixtures thereof and optionally a co-promoter selected from the group consisting of Group I, Group II, lanthanide and transition metals.

12. A process as claimed in claim 1 in which the reactor comprises a fluid-bed reactor and the catalyst comprises a fluid-bed catalyst.

13. A process as claimed in claim 7 in which the reactor comprises a fluid-bed reactor and the catalyst comprises a fluid-bed catalyst.

14. A process as claimed in claim 9 in which the reactor comprises a fluid-bed reactor and the catalyst comprises a fluid-bed catalyst.

15. A process as claimed in claim 11 in which the reactor comprises a fluid-bed reactor and the catalyst comprises a fluid-bed catalyst.

16. A process as claimed in claim 8 in which said pressure is between 6 barg and 14 barg.

17. A process as claimed in claim 16 in which said pressure is between 7 barg and 12 barg.

18. A process as claimed in claim 9 in which said pressure is between 6 barg and 14 barg.

19. A process as claimed in claim 18 in which said pressure is between 7 barg and 12 barg.

20. A process as claimed in claim 1 in which said insert gas is selected from the group consisting of nitrogen, argon and mixtures thereof.

* * * * *

UNITED STATES PATENT AND TRADEMARK OFFICE
CERTIFICATE OF CORRECTION

PATENT NO. : 6,342,628 B1
DATED : January 29, 2002
INVENTOR(S) : Williams et al.

It is certified that error appears in the above-identified patent and that said Letters Patent is hereby corrected as shown below:

Column 9,
Line 27, please replace "above 60 mol%, and up to 85 mol%" by -- 72 to 85 mol% --.

Signed and Sealed this

Second Day of September, 2003

JAMES E. ROGAN
*Director of the United States Patent and Trademark Office*